United States Patent
Eury et al.

(10) Patent No.: US 10,398,868 B2
(45) Date of Patent: Sep. 3, 2019

(54) NASAL PRONG AND PATIENT INTERFACE DEVICE INCLUDING THE SAME

(71) Applicant: KONINKLIJKE PHILIPS N.V., Eindhoven (NL)

(72) Inventors: Elizabeth Eury, Latrobe, PA (US); Kevin Daniel Himes, Irwin, PA (US); Mark Alan Sellew, Belle Vernon, PA (US); Eric Alan Higgins, Cheswick, PA (US); Michael Allan Youhouse, Gibsonia, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 565 days.

(21) Appl. No.: 14/779,625

(22) PCT Filed: Mar. 27, 2014

(86) PCT No.: PCT/IB2014/060208
§ 371 (c)(1),
(2) Date: Sep. 24, 2015

(87) PCT Pub. No.: WO2014/155329
PCT Pub. Date: Oct. 2, 2014

(65) Prior Publication Data
US 2016/0051784 A1    Feb. 25, 2016

Related U.S. Application Data

(60) Provisional application No. 61/805,605, filed on Mar. 27, 2013.

(51) Int. Cl.
  *A61M 16/00*    (2006.01)
  *A61M 16/06*    (2006.01)
  *A61F 5/34*     (2006.01)

(52) U.S. Cl.
  CPC .......... *A61M 16/0622* (2014.02); *A61F 5/34* (2013.01); *A61M 16/06* (2013.01);
  (Continued)

(58) Field of Classification Search
  CPC .......... A61M 16/0622; A61M 16/0666; A61M 16/0605; A61M 2205/0216; A61M 16/06;
  (Continued)

(56) References Cited

U.S. PATENT DOCUMENTS 4,660,555 A * 4/1987 Payton .............. A61M 16/0488
                                                  128/207.18
4,782,832 A   11/1988 Trimble
(Continued)

FOREIGN PATENT DOCUMENTS

CN    101405046 A    4/2009
CN    101468222 A    7/2009
(Continued)

OTHER PUBLICATIONS

Definition for the term "end", dictionary.com, captured on Oct. 15, 2018.*

*Primary Examiner* — Michael J Tsai
*Assistant Examiner* — Tu A Vo
(74) *Attorney, Agent, or Firm* — Michael W. Haas

(57) ABSTRACT

A nasal prong for a cushion member for use with a patient interface device that includes a casing, a flap extending from the casing for insertion into a nostril of a patient, and a bottom cap. The casing and the bottom cap define a space. A fill material is disposed in the space defined by the casing and the bottom cap, wherein the casing is structured to deform and conform to a shape of a portion of the nostril when the nostril applies pressure to the casing.

15 Claims, 10 Drawing Sheets

(52) U.S. Cl.
CPC .... *A61M 16/0605* (2014.02); *A61M 16/0616* (2014.02); *A61M 16/0666* (2013.01); *A61M 16/0683* (2013.01); *A61M 2205/0216* (2013.01)

(58) Field of Classification Search
CPC .......... A61M 16/0616; A61M 16/0627; A61M 2016/0661; A61M 16/0672; A61M 16/0677; A61M 16/0683; A61F 5/34; A61F 2/186; A62B 23/06
See application file for complete search history.

(56) References Cited

U.S. PATENT DOCUMENTS

| | | | |
|---|---|---|---|
| 5,269,296 A | 12/1993 | Landis | |
| 5,533,506 A * | 7/1996 | Wood | A61M 16/0666 128/200.26 |
| 7,210,481 B1 | 5/2007 | Lovell | |
| 8,434,485 B2 | 5/2013 | Osier | |
| 8,833,372 B2 | 9/2014 | Han | |
| 2004/0065330 A1* | 4/2004 | Landis | A61M 16/06 128/207.18 |
| 2005/0011524 A1* | 1/2005 | Thomlinson | A61M 16/0666 128/207.18 |
| 2008/0051674 A1* | 2/2008 | Davenport | A61B 5/087 600/561 |
| 2008/0142019 A1* | 6/2008 | Lewis | A61M 16/024 128/207.18 |
| 2008/0276938 A1 | 11/2008 | Jeppesen | |
| 2008/0289633 A1 | 11/2008 | Kwok | |
| 2009/0044808 A1* | 2/2009 | Guney | A61M 16/0666 128/206.24 |
| 2009/0301499 A1 | 12/2009 | Chalk | |
| 2010/0229872 A1 | 9/2010 | Ho | |
| 2011/0073116 A1* | 3/2011 | Genger | A61M 16/0666 128/207.18 |
| 2011/0125052 A1* | 5/2011 | Davenport | A61M 16/0051 600/561 |
| 2011/0232649 A1* | 9/2011 | Collazo | A61M 16/06 128/207.18 |
| 2012/0204870 A1* | 8/2012 | McAuley | A61M 16/06 128/203.12 |
| 2012/0318271 A1 | 12/2012 | Ho | |
| 2012/0318274 A1 | 12/2012 | Ho | |
| 2013/0186403 A1* | 7/2013 | Chang | A61M 16/0666 128/205.25 |
| 2017/0021121 A1 | 1/2017 | Guney | |

FOREIGN PATENT DOCUMENTS

| | | | | |
|---|---|---|---|---|
| EP | 2022528 A2 | 2/2009 | | |
| JP | 2012513870 A | 6/2012 | | |
| JP | 2012526592 A | 11/2012 | | |
| RU | 2009149208 A | 7/2011 | | |
| WO | WO2009051655 A2 | 4/2009 | | |
| WO | WO2009151344 A1 | 12/2009 | | |
| WO | WO2010131189 A1 | 11/2010 | | |
| WO | WO2011086437 A2 | 7/2011 | | |
| WO | WO 2011086438 A2 * | 7/2011 | ........ A61M 16/0666 | |

* cited by examiner

NASAL PRONG AND PATIENT INTERFACE DEVICE INCLUDING THE SAME

CROSS-REFERENCE TO RELATED APPLICATIONS

This patent application claims the priority benefit under 35 U.S.C. § 371 of international patent application no. PCT/IB2014/060208, filed Mar. 27, 2014, which claims the priority benefit under 35 U.S.C. § 119(e) of U.S. Provisional Application No. 61/805,605 filed on Mar. 27, 2013, the contents of which are herein incorporated by reference.

BACKGROUND OF THE INVENTION

1. Field of the Invention

The present invention pertains to patient interface devices for delivering a flow of breathing gas to a patient during, for example, respiratory therapy, and, in particular, to nasal prongs adapted for use with patient interface devices.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

One method for treating OSA is positive airway pressure (PAP) therapy. Known PAP therapies include continuous positive airway pressure (CPAP), wherein a constant positive airway pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Another concern is that an improperly fitted patient interface device can include gaps between the patient interface device and the patient that cause unwanted leakage. Thus, it is desirable to select a patient interface device that properly fits a patient.

One type of patient interface device is a nasal pillows mask. Typically, nasal pillows masks use a silicone sealing cushion having silicone nasal prongs that are received within the patient's nares to seal in and around the opening of the nares. However, silicone nasal prongs may not provide optimal comfort for the patient.

SUMMARY OF THE INVENTION

Accordingly, it is an object of the present invention to provide a patient interface device that overcomes the shortcomings of conventional patient interface devices. This object is achieved according to one embodiment of the present invention by providing a nasal prong for a cushion member adapted for use with a patient interface device, wherein the nasal prong advantageously deforms to form a seal with a nostril of the patient.

In one embodiment, a nasal prong for a cushion member adapted for use with a patient interface device is provided. The nasal prong includes a casing, a flap extending from the casing and being adapted to be inserted into a nostril of a patient, a bottom cap, wherein the casing and the bottom cap define a space, and a fill material disposed in the space defined by the casing and the bottom cap, wherein the casing is structured to deform and conform to a shape of a portion of the nostril when the nostril applies pressure to the casing.

In another embodiment, a nasal prong for a cushion member adapted for use with a patient interface device is provided, The nasal prong includes a casing, a first flap extending from the casing and being adapted to be inserted into a nostril of a patient, a bottom cap, wherein the casing and the bottom cap define a space, a fill material disposed in the space defined by the casing and the bottom cap, and a second flap disposed between the casing and the nostril of the patient, wherein the casing is structured to deform and conform to a shape of a portion of the nostril and press against the second flap when the nostril applies pressure to the casing causing the second flap to conform to and to form a seal with the nostril of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
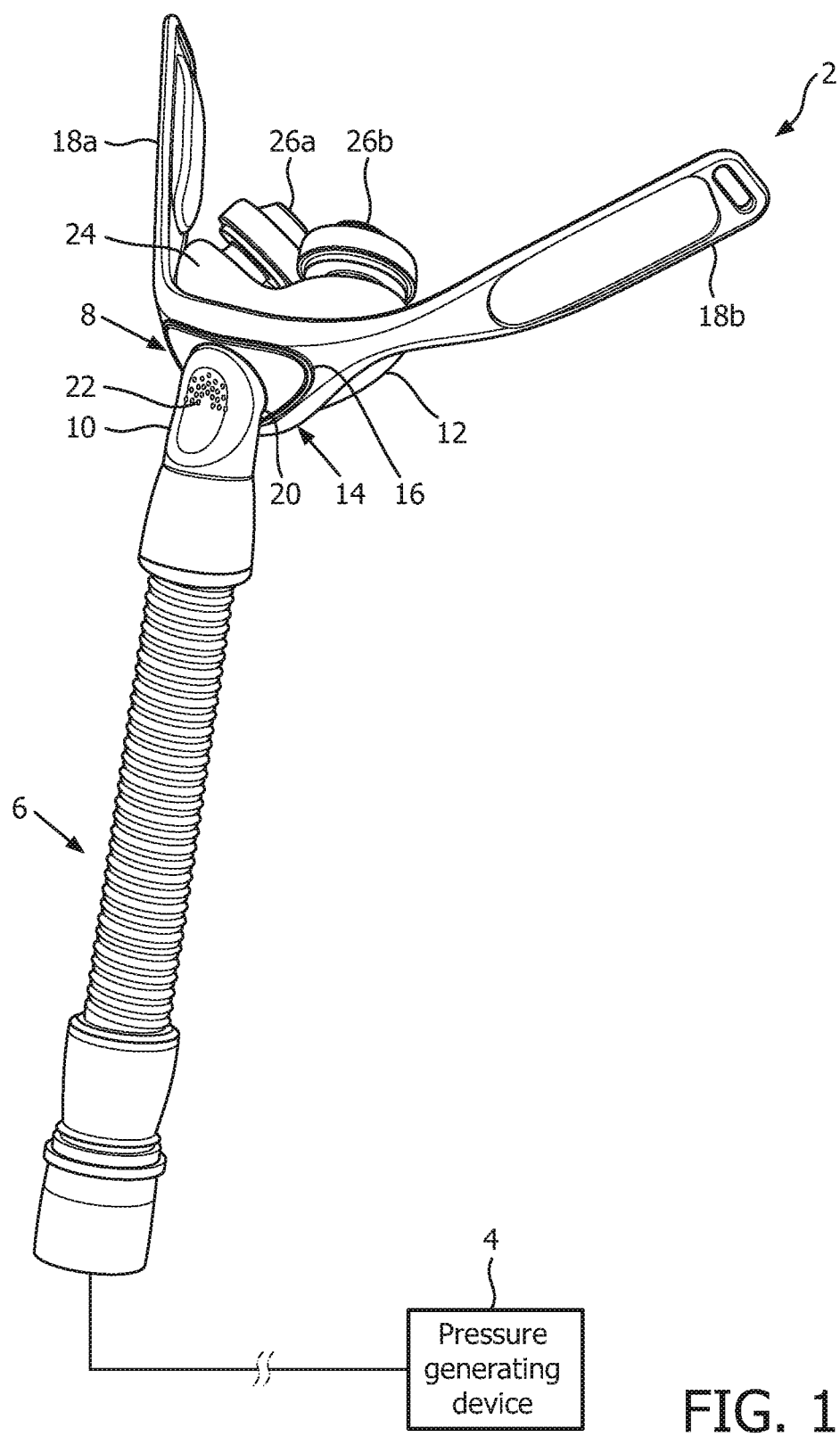
FIG. 1 is a perspective view of a patient interface device in accordance with an embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8 including an elbow conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are typically collectively referred to as a patient circuit.

In the present embodiment (described in detail herein), patient interface device 8 comprises a pillows style nasal cushion having nasal prongs that are received within the patient's nares in order to deliver breathing gas to the airway of the patient through the patient's nose. In the exemplary embodiment shown in FIG. 1, patient interface device 8 includes a cushion member 12 and a frame member 14 having a faceplate portion 16 and arms 18a and 18b. Cushion member 12 is coupled to a rear side of frame member 14.

Frame member 14 is made of a rigid or semi-rigid material, such as, without limitation, an injection molded thermoplastic or silicone. Straps (not shown) of a headgear component may be attached to arms 18a and 18b to secure patient interface device 8 to the patient's head. An opening 20 in faceplate portion 16 to which elbow conduit 10 is coupled allows the flow of breathing gas from pressure generating device 4 to be communicated to an interior space defined by cushion member 12, and then, to the airway of a patient. Opening 20 in faceplate portion 16 also allows the flow of exhalation gas (from the airway of such a patient) to be communicated to exhaust vent 22 provided in elbow conduit 10.

As seen in FIG. 1, cushion member 12 includes a main body portion 24 and two nasal prongs 26a,26b coupled to main body portion 24. The structure of nasal prongs 26a,26b and main body portion 24 will be discussed in further detail below in conjunction with a number of exemplary embodiments of the disclosed concept.

Figure 2:
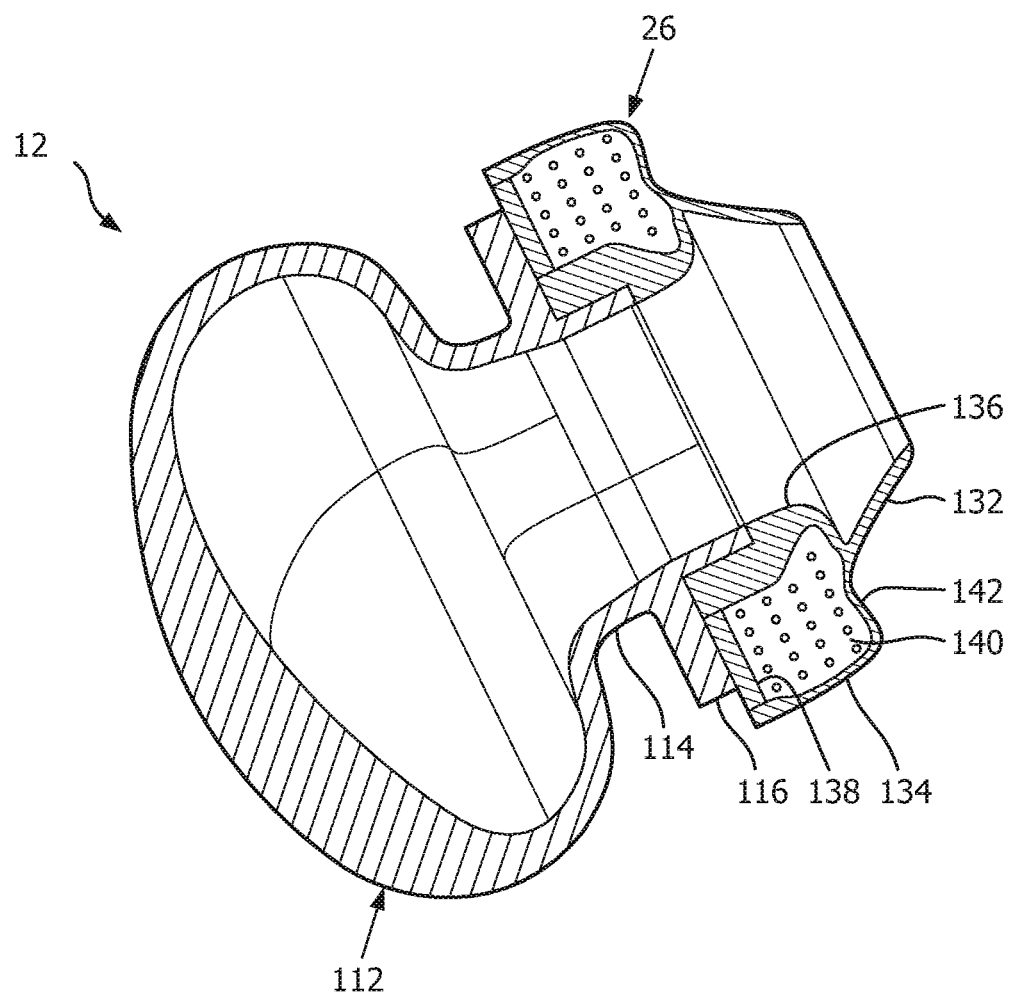
FIG. 2 is a cross-sectional view of a cushion member of the patient interface device of FIG. 1.

FIG. 2 illustrates a cross-section of cushion member 12 according to an exemplary embodiment. Referring to FIG. 2, cushion member 12 includes main body portion 24 that comprises a base 112, two stems 114, and two platforms 116 (only one such stem 114 and platform 116 is shown in the cross-section of FIG. 2). Base 112, stems 114, and platforms 116 are integrally formed together. Main body portion 24 of cushion member 12 can be made from any suitable material, such as gel, silicone, foam, rubber, or a combination of materials. Nasal prongs 26a,26b are coupled to corresponding platforms 116 of cushion member 12.

Apertures formed by nasal prongs 26a,26b allow air to flow from a patient into a chamber formed inside cushion member 12. Air flow between the hollow area inside cushion member 12 and delivery conduit 6 is facilitated by an opening 111 (see FIG. 7) formed in cushion member 12.

Continuing to refer to FIG. 2, nasal prong 26 (26a or 26b) includes a flap 132, outer casing 134, inner casing 136, and bottom cap 138. Flap 132, outer casing 134, inner casing 136, and bottom cap 138 can each be made from any suitable material, such as gel, silicone, foam, rubber, or a combination of materials. In one exemplary embodiment, flap 132 is made from silicone. Flap 132 is adapted to be inserted into a nostril of the user. Outer casing 134 is disposed on an outer portion of nasal prong 26 and inner casing 136 is disposed on an inner portion of nasal prong 26. Outer casing 134, inner casing 136, and bottom cap 138 form a space which is filled with a fill material 140. Fill material 140 generally consists of a gel or other suitable material that generally conforms to the space formed by outer casing 134, inner casing 136, and bottom cap 138.

Fill material 140 may be a viscoelastic material, such as a gel substance comprising a viscoelastic polyurethane polymer, or an elastic material. Fill material 140 may also be liquid or air. As used herein, the term viscoelastic material shall mean a material that exhibits both viscous and elastic characteristics when undergoing deformation, and as a result exhibits time dependent strain. A viscoelastic material will thus deform under the influence of an applied stress, and when the stress is removed from the material, the material will slowly and not instantaneously recover from at least a portion of the deformation. As used herein, the term elastic material shall mean a material that exhibits elastic but not viscous characteristics when undergoing deformation. Elastic materials deform under the influence of an applied stress and return instantaneously to their original state once the stress is removed, thereby recovering from all of the deformation.

Cushion member 12 is adapted such that when the user wears patient interface device 8, the user's nostril presses against outer casing 134. In turn, interaction between base 112 and stem 114 creates a spring force which presses nasal prong 26 back against the user's nostril. The amount of spring force generated increases the further stems 114 are depressed into base 112. Base 112 and stems 114 generate a spring force in a range of about 20 to 250 grams. The spring force assists with allowing nasal prong 26 to conform to the user's nostril and create a seal.

Figure 3A:
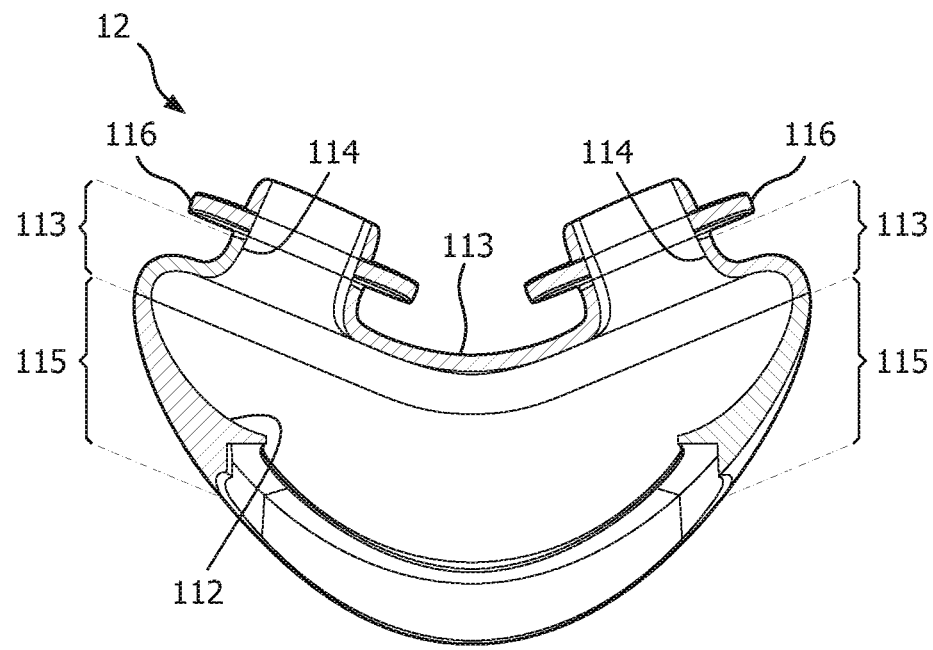
FIGS. 3A and 3B are additional cross-sectional views of the cushion member of FIG. 2.
Figure 3B:
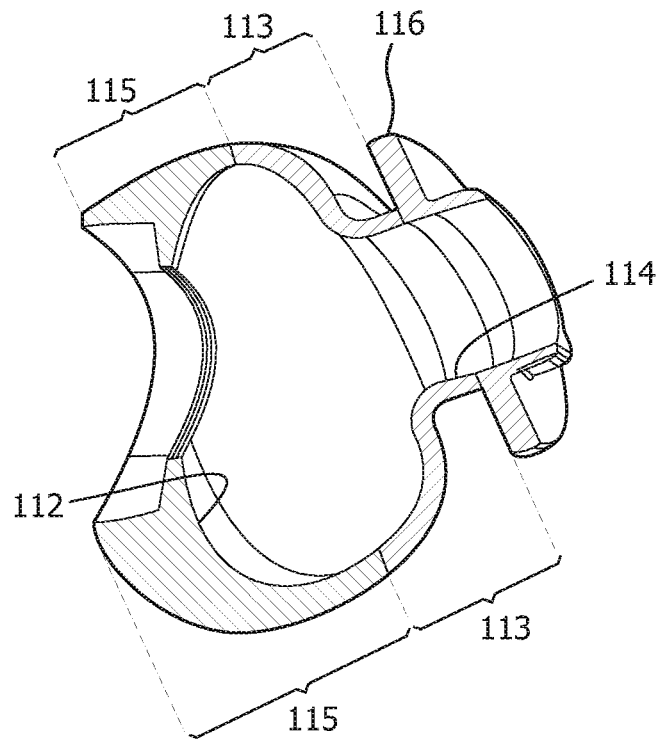

In some embodiments of the disclosed concept, base 112 and stems 114 have a durometer in a range of about 10 shA to 50 shA. Referring now to FIGS. 3A and 3B, the variable thickness of base 112 and stems 114 is described in more detail. For purposes of illustration, base 112 and stems 114 are divided into a first region 113 and a second region 115. First region 113 begins at an end of stems 114 adjacent to platforms 116 and extends partially into base 112. The remaining portion of base 112 forms second region 115. First region 113 is thinnest in the area adjacent to platforms 116 and thickest in the area adjacent to second region 115. In some embodiments of the disclosed concept, the thicknesses of cushion member 12 in first region 113 are within a range of about 0.4-1.8 mm thick. In some embodiments of the disclosed concept, the thicknesses of cushion member 12 in second region 115 are within a range of about 0.8-5.0 mm thick.

Cushion member 12 incorporates an arched structure that transfers compressive load through its sidewalls to its outside perimeter and away from sensitive areas of the user's philtrum and septum as well as away from the airpath through cushion member 12. Greater thicknesses in second region 115 provides structural support for cushion member 12 which increases resistance to a complete collapse of cushion member 12. A complete collapse of cushion member 12 happens when stem 114 collapses into base 112 far enough to block airflow through cushion member 12. Thicknesses of the walls of cushion member 12 gradually decrease from in the direction from second region 115 to first region 113 which avoids an abrupt transition in the modulus of cushion member 12. The gradual transition in thicknesses mitigates the potential for pressure points and aids in controlling conformance of cushion member 12. The transition to thinner walls also helps enhance the stability of cushion member 12.

Referring back to FIG. 2, a depression 142 is formed in an area of outer casing 134. Depression 142 is operable to facilitate deformation of outer casing 134 allowing to conform to a shape of the user's nostril when pressure is applied to outer casing 134 by the user's nostril, as will be described in more detail hereinafter with respect to FIGS. 4A and 4B.

Figure 4A:
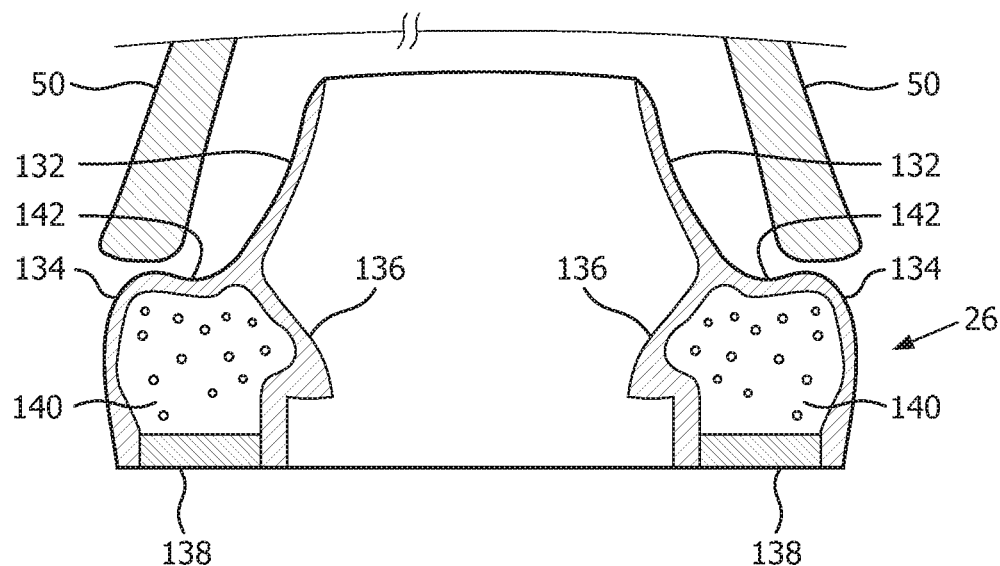
FIGS. 4A-4F are cross-sectional views of a nasal prong in accordance with an embodiment of the disclosed concept.
Figure 4B:
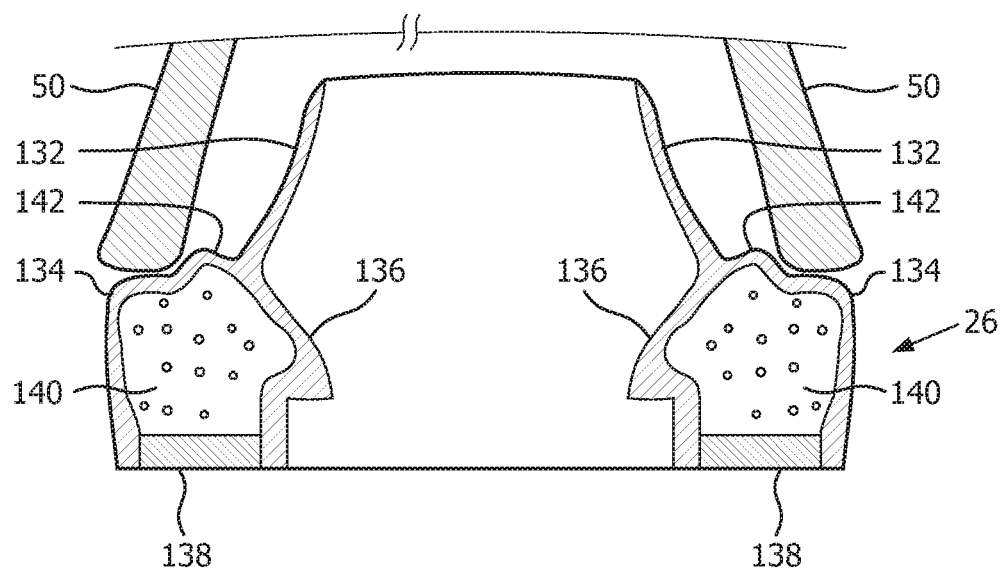

FIGS. 4A and 4B illustrate cross-sections of a nasal prong 26 in accordance with an embodiment of the disclosed concept. In FIG. 4A, nasal prong 26 is illustrated when a nostril 50 of a user is not applying pressure to nasal prong 26. In FIG. 4B, nostril 50 is applying pressure to the nasal prong 26, such as, for example, when the user is wearing patient interface device 8.

Referring to FIG. 4A, depression 142 is formed in an area of outer casing 134 adjacent to an area where the nostril 50 applies pressure to outer casing 134. Depression 142 may be, for example and without limitation, a sink or divot formed in outer casing 134 which makes outer casing 134. Depression 142 increases the perimeter of the space formed by outer casing 134, inner casing 136, and bottom cap 138 relative to its cross-sectional area, which increases the ability of the outer casing 134 deform when pressure is applied to it without immediately putting it in tension. In contrast, if the outer casing 134, inner casing 136, and bottom cap 138 formed a semi-circular shape which minimized the perimeter of the space with respect to its cross-sectional area, the outer casing 134 would be resistant to deformation and would be immediately put in tension when pressure is applied to it.

Turning now to FIG. 4B, nostril 50 is applying pressure to nasal prong 26, and more specifically, to outer casing 134. As shown in FIG. 4B, outer casing 134 deforms and conforms to the shape of nostril 50 when nostril 50 applies pressure. In more detail, outer casing 134 collapses in the area where nostril 50 applies pressure, which causes a portion of fill material 140 to be displaced. Outer casing 134 expands in the area of depression 142 to accommodate the displaced fill material 140. By collapsing in the area where nostril 50 applies pressure and expanding in the adjacent area where depression 142 is formed, outer casing 134 conforms to the shape of nostril 50, as shown in FIG. 4B, thereby creating an improved seal between nasal prong 26 and nostril 50.

Figure 4C:
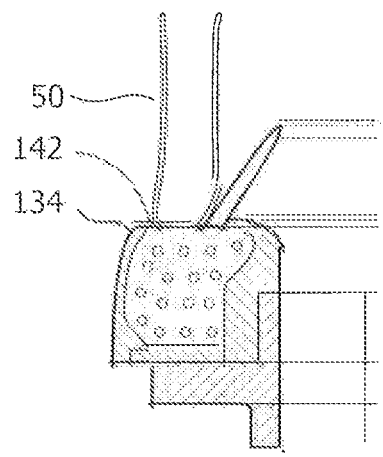
Figure 4D:
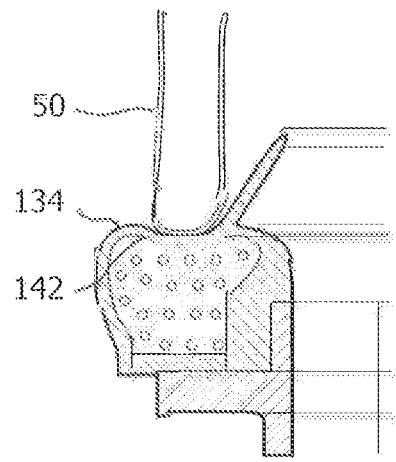
Figure 4E:
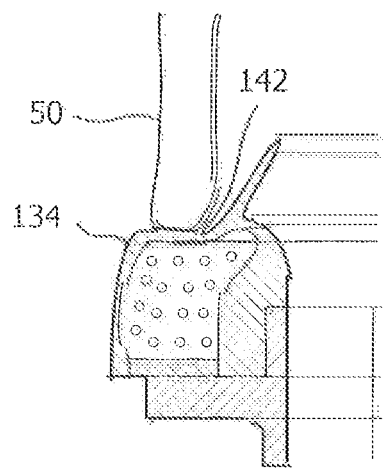
Figure 4F:
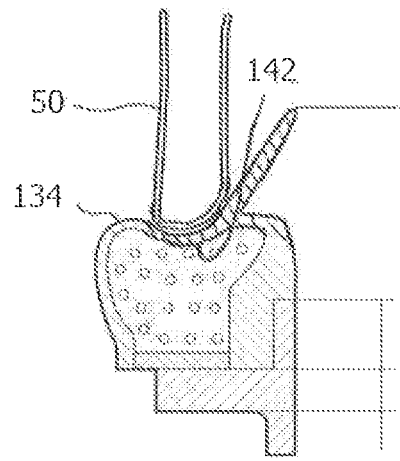

Nostrils 50 of users can vary in size and shape, as well as where they apply pressure to outer casing 134. The amount of pressure applied by nostril 50 can also vary. These variations can change the manner in which outer casing 134 deforms. Despite these variations, outer casing 134 deforms to conform to the shape of nostril 50 and forms a seal with nostril 50. For example, FIGS. 4C-F illustrate alternative styles of deformation of outer casing 134. Referring to FIGS. 4C and 4D, nostril 50 applies pressure to the area of outer casing 134 where depression 142 is formed. Depression 142 becomes a pocket for nostril 50 to sit in and outer casing 134 deforms to conform to the shape of inner and outer sides of nostril 50, as shown in FIG. 4D. Referring to FIGS. 4E and 4F, nostril 50 applies pressure to an area just outside depression 142. In response, outer casing 134 deforms to conform to the shape of inner and outer sides of nostril 50, as shown in FIG. 4F.

Figure 5A:
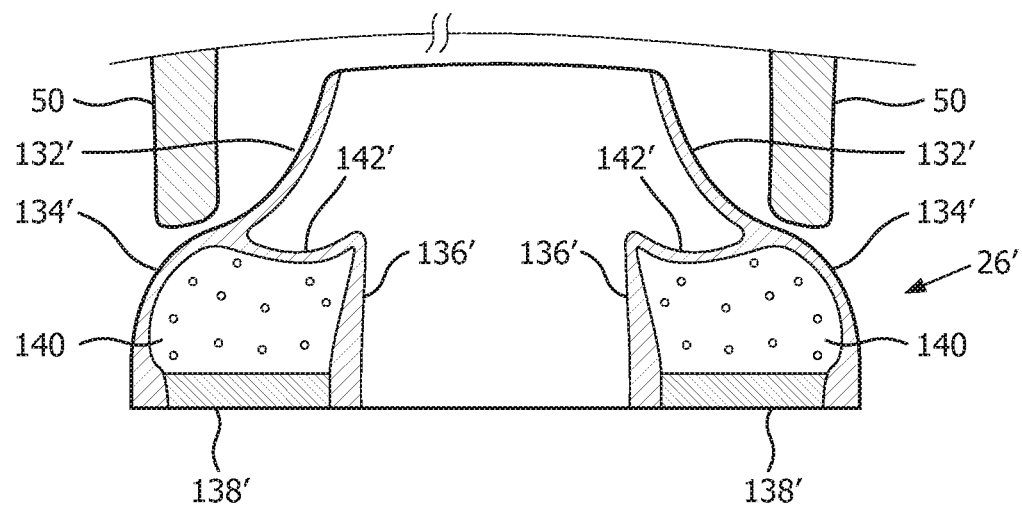
FIGS. 5A and 5B are cross-sectional views of a nasal prong in accordance with another embodiment of the disclosed concept.
Figure 5B:
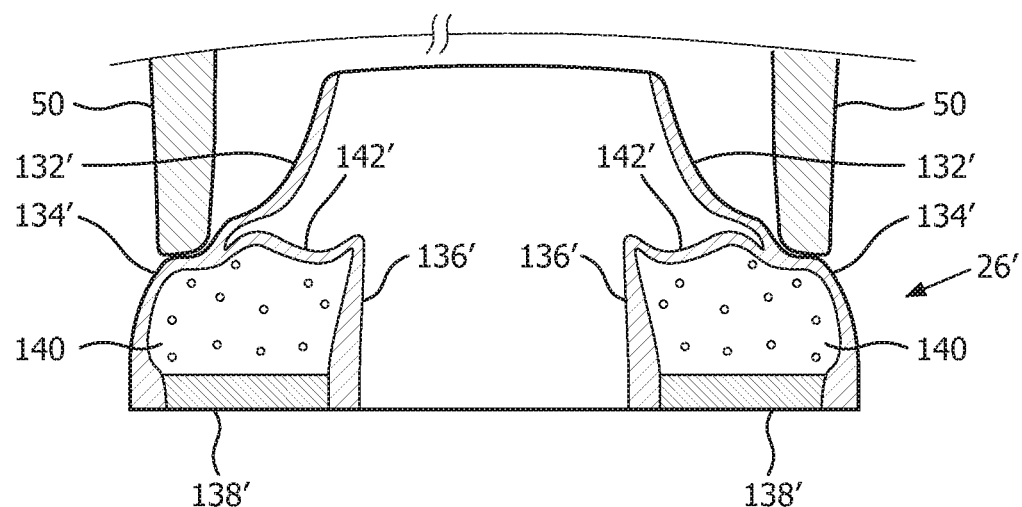

FIGS. 5A and 5B illustrate cross-sections of a nasal prong 26' in accordance with an alternative exemplary embodiment of the disclosed concept. It will be appreciated by those having ordinary skill in the art that nasal prong 26' may be adapted for use with patient interface device 8 without departing from the scope of the disclosed concept. In FIG. 5A nasal prong 26' is illustrated when nostril 50 is not applying pressure to nasal prong 26'. In FIG. 4B, nostril 50 is applying pressure to nasal prong 26'.

Referring to FIG. 5A, depression 142' is formed in an area of inner casing 136' adjacent to an area of outer casing 134' that nostril 50 will apply pressure to. Depression 142' may be, for example and without limitation, a sink or divot formed in inner casing 136' which makes inner casing 136'.

Turning now to FIG. 5B, nostril 50 is applying pressure to nasal prong 26', and more specifically, to an area of outer casing 134'. As shown in FIG. 5B, outer casing 134' deforms by collapsing in the area where nostril 50 applies pressure, which causes a portion of fill material 140 to be displaced. Inner casing 136' expands in the area of depression 142' to accommodate the displaced fill material 140. By collapsing in the area where nostril 50 applies pressure, outer casing 134' conforms to the shape of nostril 50. Inner casing 136' also conforms to the shape of nostril 50 and presses against flap 132' causing flap 132' to also conform to the shape of nostril 50, thereby creating an improved seal between nasal prong 26' and nostril 50.

Figure 6A:
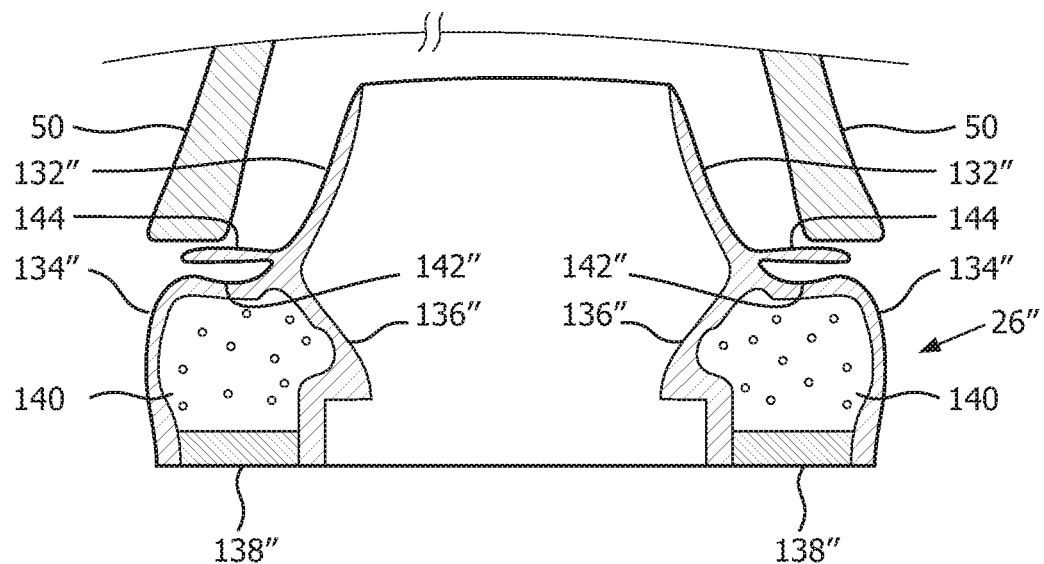
FIGS. 6A and 6B are cross-sectional views of a nasal prong in accordance with another embodiment of the disclosed concept.
Figure 6B:
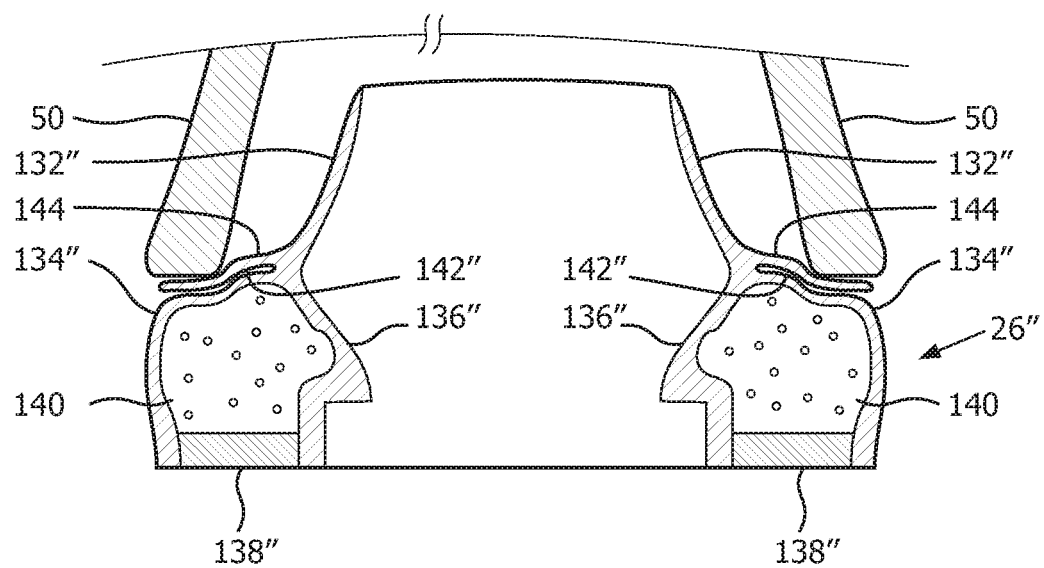

FIGS. 6A and 6B illustrate cross-sections of a nasal prong 26" in accordance with yet another alternative exemplary embodiment of the disclosed concept. It will be appreciated by those having ordinary skill in the art that nasal prong 26" may be adapted for use with patient interface device 8 without departing from the scope of the disclosed concept. In FIG. 6A nasal prong 26" is illustrated when nostril 50 is not applying pressure to nasal prong 26". In FIG. 6B, nostril 50 is applying pressure to nasal prong 26".

Referring to FIG. 6A, nasal prong 26" includes a second flap 144 formed between outer casing 134" and nostril 50. In one particular embodiment, second flap 144 is made of silicone, but it is appreciated that second flap 144 may be made of any suitable material without departing from the scope of the disclosed concept. Depression 142" is formed in an area of outer casing 134" adjacent to an area where nostril 50 will apply pressure. Depression 142" may be, for example and without limitation, a sink or divot formed in outer casing 134" which makes outer casing 134".

Turning now to FIG. 6B, nostril 50 is applying pressure to nasal prong 26", and more specifically, to outer casing 134" through second flap 144. As shown in FIG. 6B, second flap 144 is pressed by nostril 50 against outer casing 134" causing outer casing 134" to deform by collapsing in the area where pressure is applied, thus causing a portion of fill material 140 to be displaced. In the area of depression 142", outer casing 134" expands to accommodate the displaced fill material 140. The expansion of outer casing 134" in the area of depression 142" causes outer casing 134" to conform to the shape of nostril 50 and to press against second flap 144 and cause second flap 144 to conform to the shape of nostril 50, thereby creating an improved seal between nasal prong 26" and nostril 50.

While nasal prongs 26,26',26" include depressions 142, 142',142", it will also be appreciated by one having ordinary skill in the art that other variations in geometry may be used to increase the perimeter of the spaces defined by outer casing 134,134',134", inner casing 136,136',136", and bottom caps 138,138',138" relative to their cross-sectional areas to increase the deformability of the outer casings 134,134', 134" without departing from the scope of the disclosed concept.

Figure 7:
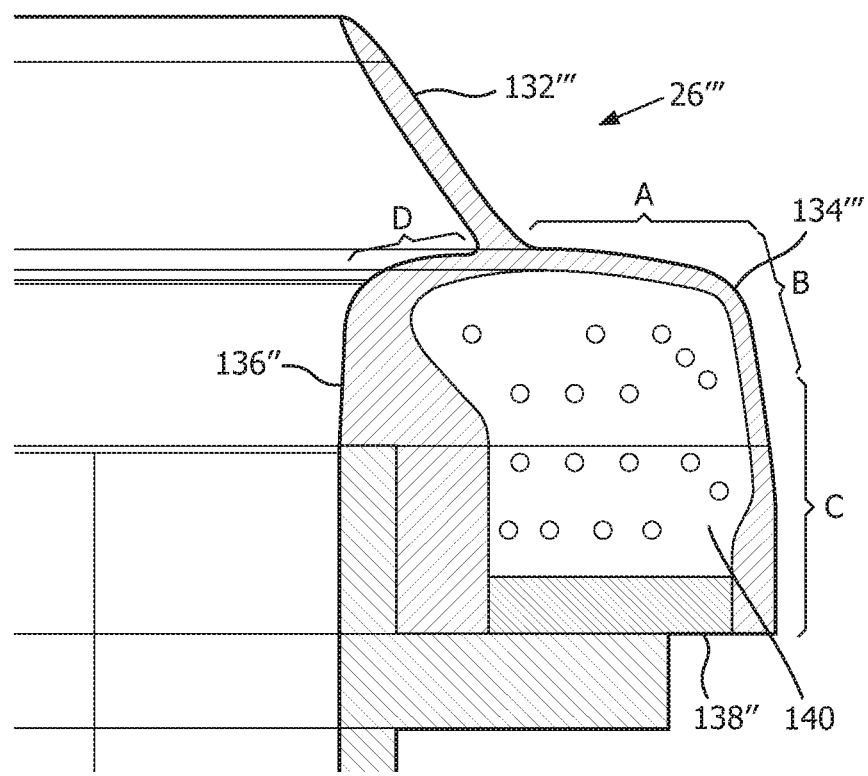
FIG. 7 is a cross-sectional view of a nasal prong in accordance with another embodiment of the disclosed concept.

FIG. 7 illustrates a cross section of a portion of a nasal prong 26'" in accordance with another embodiment of the disclosed concept. It will be appreciated by those having ordinary skill in the art that nasal prong 26" may be adapted for use with patient interface device 8 without departing from the scope of the disclosed concept. Inner casing 136'" and/or outer casing 134'" of nasal prong 26'" are formed of a material that can be elongated under tension. When nostril 50 applies pressure to outer casing 134'", outer casing 134'" deforms to conform to the shape of nostril 50 to form a seal with nostril 50. Inner casing 136'" and/or outer casing 134'" elongate to accommodate fill material 140 displaced due to the deformation. As such, outer casing 134'" is able to conform to the shape of and form a seal with nostril 50 without having a depression formed therein.

Variations in thickness of inner casing 136'" and outer casing 134'" influence where deformation occurs as well as provide structural support. For example, inner casing 136'" and outer casing 134'" are divided into regions A, B, C, and D. Region A is the thinnest and deformation is most likely to occur in region A. Regions B and D are slightly thicker than Region A. Region C is thickest and provides structural support to outer casing 134'". In some embodiments, the thickness of Region A is in a range of about 0.2-0.3 mm, the thickness of Regions B and D are in a range of about 0.2-0.4 mm, and the thickness of Region C is in a range of about 0.4-0.6 mm. It will be appreciated by one having ordinary skill in the art that variations in thickness can also be applied to any of nasal prongs 26,26',26" without departing from the scope of the disclosed concept.

Figure 8:
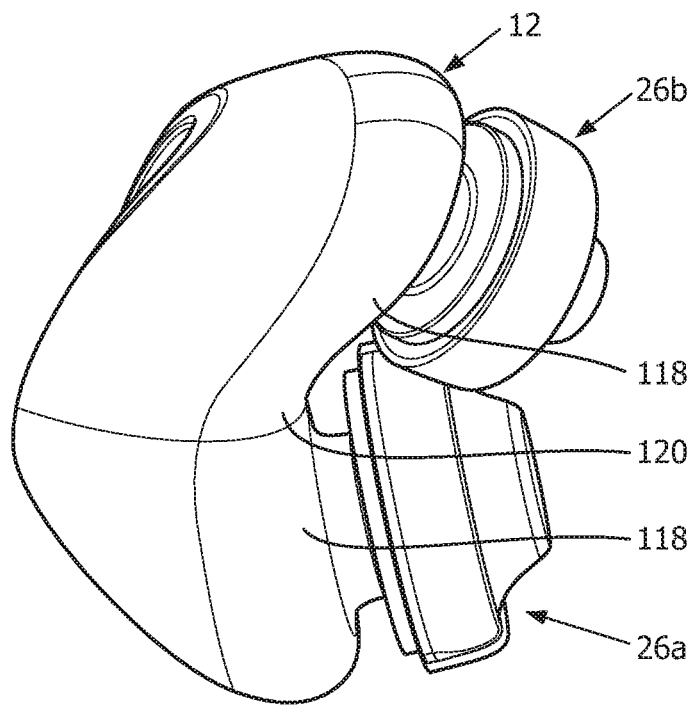
FIG. 8 is a perspective view of a bottom side of a cushion of the patient interface device of FIG. 1.

FIG. 8 is a view illustrating a bottom side of cushion member 12. The bottom side of cushion member 12 is adapted to conform to and rest on the user's upper lip when the user wears patient interface device 8. To facilitate resting on the user's upper lip, cushion member 12 includes upper lip contacting portions 118 and upper lip relief portion 120. Cushion member 12 is adapted such that upper lip contacting portions 118 contact the user's upper lip in areas outside the middle area of the user's upper lip. Upper relief portion 120 is curved to relieve pressure applied to the middle area of the user's upper lip and conforms to the user's Philtrum (i.e., the section between the upper lip and Septum). The middle area of the upper lip is a more sensitive area of the upper lip, and relieving pressure to this area increases comfort for the user. The conformance of the cushion member 12 also provides a low profile design that contours to the user and increases stability. The conformance of cushion member 12 to the user's upper lip further aids, in conjunction with the variations in thickness of cushion member 12 previously described, in preventing cushion member 12 from collapsing and blocking the air path through cushion member 12 when the user tightens the headgear assembly on patient interface device 8.

In some embodiments of the disclosed concept, upper lip contacting portions 118 and upper lip relief portion 120 are thinner than other areas of cushion member 12. The thinner thickness of upper lip contacting portions 118 and upper lip relief portion 120 provide additional comfort for the user by having more compliance in the structure, which is thinner, thereby decreasing modulus and allowing it to be more flexible.

Figure 9:
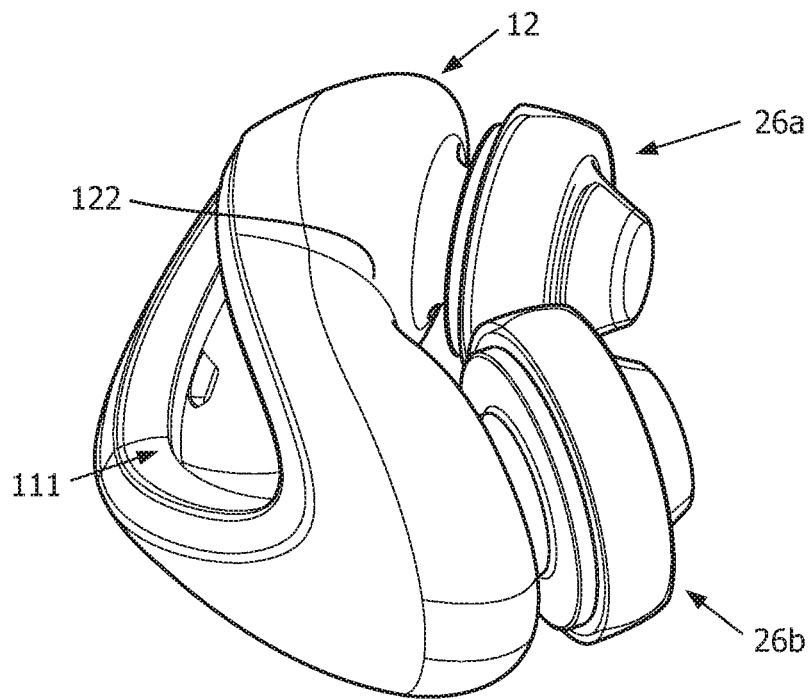
FIG. 9 is a perspective view of a top side of the cushion of the patient interface device of FIG. 1.

FIG. 9 is a view illustrating a top side of cushion member 12. The top side of cushion member 12 is disposed near the tip of the user's nose when the user wears patient interface device 8. The tip of the user's nose is a sensitive area and undue pressure can cause discomfort for the user. The top side of cushion member 12 includes a nose relief portion 122 which is curved so as to prevent or relieve the pressure applied to the user's nose, thus increasing the user's comfort.

Figure 10:
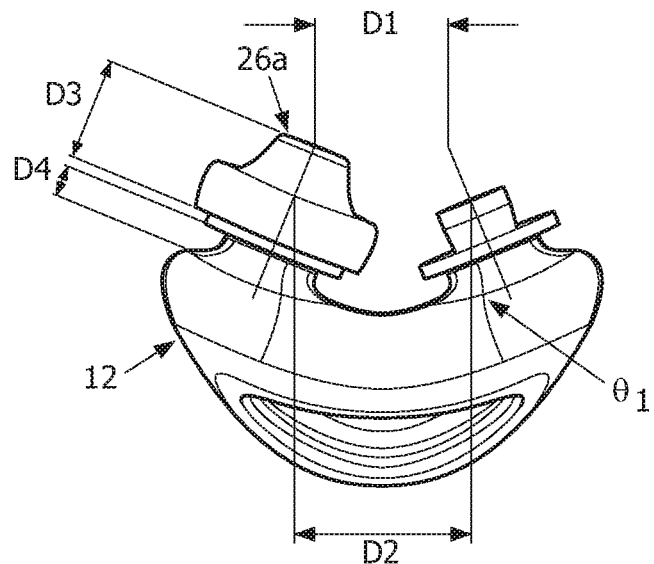
FIG. 10 is a top view of a patient interface portion in accordance with an embodiment of the disclosed concept.

FIG. 10 illustrates a top view of cushion member 12. In FIG. 8, D1 is a distance between the centers of the tips of nasal prongs 26a,26b (nasal prong 26b is not shown in FIG. 10). In some embodiments of the disclosed concept, D1 is in a range of about 15-20 mm, and is preferably selected from one of about 16 mm, 17.5 mm, 19.5 mm D2 is a distance between the centers of the tips of platforms 416. In some embodiments of the disclosed concept, D2 is in a range of about 20-25 mm, and is preferably selected from one of about 20.5 mm, 22 mm, and 24 mm D3 is a height of nasal prongs 26a,26b. In some embodiments of the disclosed concept, D3 is in a range of about 9-12 mm, and is preferably about 10.6 mm D4 is a height of stem 114. In some embodiments of the disclosed concept, D4 is in a range of about 2-4 mm, and is preferably about 3 mm. $\theta_1$ is an angle between an axis of one of nasal prongs 26a,26b and a line parallel to a center line of cushion member 12. In some embodiments of the disclosed concept, $\theta_1$ is in a range of about 20-24°, and is preferably about 22°. In some embodiments of the disclosed concept, the overall stem height (i.e., a distance from the base of the stem to the tip of the nasal prong 26a or 26b) is in a range of about 14-16 mm, and is preferably about 15.1 mm.

Figure 11:
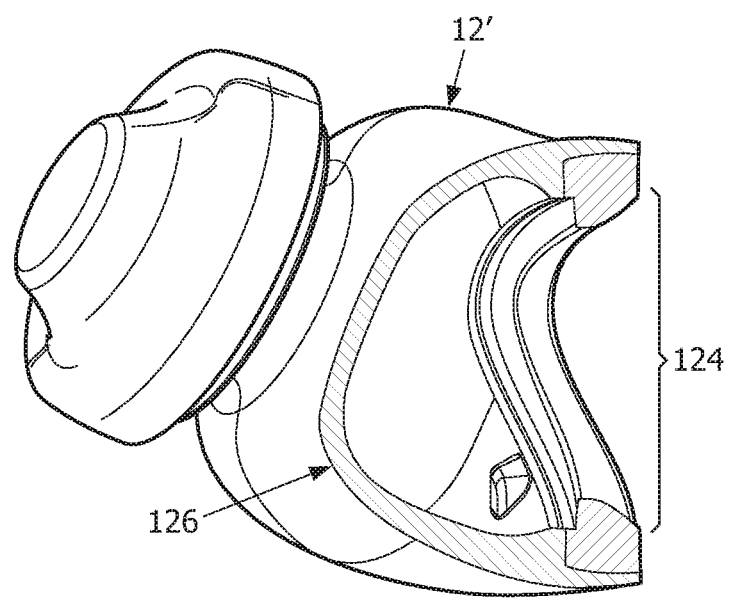
FIG. 11 is a cross-sectional view of a cushion in accordance with another exemplary embodiment of the disclosed concept.

FIG. 11 illustrates a side view of cushion member 12' in accordance with an exemplary embodiment of the disclosed concept. Cushion member 12' includes a first portion 124 made of a first material (e.g., without limitation, silicone having a durometer of about 75 shA) and a second portion 126 made of a second material (e.g., without limitation, silicone having a durometer of about 20 shA). The durometer of the first material is higher than the durometer of the second material. First portion 124 of cushion member 12' forms a portion of cushion member 12' that couples to frame member 14. Using a higher durometer material for first portion 124 of cushion member 12' allows for better audible and tactile feedback during assembly of patient interface device 8 which makes it more obvious to the user when cushion member 12' and frame member 14 are properly coupled together. The higher durometer material also creates a more robust seal between cushion member 12' and frame member 14. Furthermore, the higher durometer material helps opening 111 of cushion member 12' retain its shape. Opening 111 may have a distinctive shape, such as, for example, a triangle, which only allows cushion member 12' and frame member 14 to be coupled when they are properly aligned with each other.

Second portion 126 of cushion member 12' forms a portion of cushion member 12' that contacts the user's face. Using a lower durometer material for second portion 126 of cushion member 12' provides increased comfort for the user and also allows cushion member 12' to better conform to the user's face such as, for example, during static and dynamic moments of sleep.

Cushion member 12' having materials with different durometers may be manufactured using any suitable method without departing from the scope of the disclosed concept. In one example, the higher durometer portion of the cushion member 12' is molded first and then the lower durometer portion of cushion member 12' is overmolded onto the higher durometer portion. In another example, both the higher durometer and lower durometer portions of cushion member 12' are simultaneously formed using a two-shot molding process.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A nasal prong for a cushion member adapted for use with a patient interface device, the nasal prong comprising:
   a casing;
   a flap extending from the casing and being adapted to be inserted into a nostril of a patient;
   a bottom cap, wherein the casing and the bottom cap form an enclosed space; and
   a fill material disposed in the enclosed space formed by the casing and the bottom cap, wherein the casing is structured to deform and conform to a shape of a portion of the nostril when the nostril applies pressure to the casing, and wherein the fill material includes at least one of a gel material or a liquid material,
   wherein the casing includes a depression formed therein, wherein the casing is structured such that a first end of the depression is a first distance from the bottom cap, a second end of the depression is a second distance from the bottom cap, and a central point of the depression is a third distance from the bottom cap, wherein the central point of the depression is equidistant from the first and second ends of the depression, wherein the casing is structured such that the first and second distances are both greater than the third distance when pressure is not applied to the casing, wherein the first end or the second end of the depression is located at a point where the casing meets the flap, and wherein the flap extends from the casing in a direction away from the enclosed space and does not form any of an outer perimeter of the enclosed space.

2. The nasal prong of claim 1, wherein the casing comprises an outer casing disposed on an outer portion of the nasal prong; and an inner casing disposed on an inner portion of the nasal prong.

3. The nasal prong of claim 2, wherein the depression is formed in the outer casing.

4. The nasal prong of claim 3, wherein the casing is structured such that when the nostril of the patient applies pressure to the outer casing, the outer casing conforms to and forms a seal with the nostril of the patient.

5. The nasal prong of claim 3, further comprising a second flap disposed between the outer casing and the nostril of the patient, wherein the casing is structured such that when the nostril of the patient applies pressure to the outer casing, the outer casing conforms to the nostril of the patient and presses against the second flap to cause the second flap to conform to and to form a seal with the nostril of the patient.

6. The nasal prong of claim 2, wherein the depression is formed in the inner casing.

7. The nasal prong of claim 6, wherein the casing is structured such that when the nostril of the patient applies pressure to the outer casing, the inner casing conforms to the nostril of the patient and presses against the flap to cause the flap conform to and to form a seal with the nostril of the patient.

8. The nasal prong of claim 1, wherein at least a portion of the casing is formed from a material that allows elongation, and wherein the casing is structured such that when the nostril of the patient applies pressure to the casing, the casing elongates to conform to the nostril of the patient.

9. The nasal prong of claim 1, wherein the casing is structured to conform to a shape of at least one of an inner surface of the nostril and a surface of the patient's nose outside the nostril.

10. The nasal prong of claim 1, wherein the fill material is a viscoelastic or elastic material.

11. A patient interface device comprising:
    a cushion member having a nasal prong comprising:
        a casing;
        a flap extending from the casing and being adapted to be inserted into a nostril of a patient;
        a bottom cap, wherein the casing and the bottom cap form an enclosed space; and
        a fill material disposed in the enclosed space formed by the casing and the bottom cap, wherein the casing is structured to deform and conform to a shape of a portion of the nostril when the nostril applies pressure to the casing, and wherein the fill material includes at least one of a gel material or a liquid material, wherein the casing includes a depression formed therein, wherein the casing is structured such that a first end of the depression is a first distance from the bottom cap, a second end of the depression is a second distance from the bottom cap, and a central point of the depression is a third distance from the bottom cap, wherein the central point of the depression is equidistant from the first and second ends of the depression, wherein the casing is structured such that the first and second distances are both greater than the third distance when pressure is not applied to the casing, wherein the first end or the second end of the depression is located at a point where the casing meets the flap, and wherein the flap extends from the casing in a direction away from the enclosed space and does not form any of an outer perimeter of the enclosed space.

12. The patient interface device of claim 11, wherein the cushion member comprises a pair of upper lip contacting portions adapted to contact areas outside a middle of a patient's upper lip, and an upper lip relief portion adapted to reduce pressure applied to the middle of the patient's upper lip by the cushion.

13. The patient interface device of claim 11, wherein the cushion member comprises a nose relief portion adapted to reduce pressure applied to a patient's nose by the cushion.

14. The patient interface device of claim 11, wherein the cushion member comprises:
   a first portion formed from a first material and adapted to couple with a frame member; and
   a second portion formed from a second material and adapted to contact the patient's face, wherein a hardness of the first material is greater than a hardness of the second material.

15. A nasal prong for a cushion member adapted for use with a patient interface device, the nasal prong comprising:
   a casing;
   a first flap extending from the casing and being adapted to be inserted into a nostril of a patient;
   a bottom cap, wherein the casing and the bottom cap form an enclosed space;
   a fill material disposed in the enclosed space defined by the casing and the bottom cap; and
   a second flap disposed between the casing and the nostril of the patient, wherein the casing is structured to deform and conform to a shape of a portion of the nostril and press against the second flap when the nostril applies pressure to the casing causing the second flap to conform to and to form a seal with the nostril of the patient, wherein the casing includes a depression formed therein, wherein the casing is structured such that a first end of the depression is a first distance from the bottom cap, a second end of the depression is a second distance from the bottom cap, and a central point of the depression is a third distance from the bottom cap, wherein the central point of the depression is equidistant from the first and second ends of the depression, wherein the casing is structured such that the first and second distances are both greater than the third distance when pressure is not applied to the casing, wherein the first end or the second end of the depression is located at a point where the casing meets the first flap, and wherein the first flap does not define the enclosed space, and wherein the first flap extends from the casing in a direction away from the enclosed space and does not form any of an outer perimeter of the enclosed space.

* * * * *